United States Patent
Cerda-Moya (10) Patent No.: US 10,913,974 B2
(45) Date of Patent: Feb. 9, 2021

(54) NUCLEIC ACID AMPLIFICATION AND DETECTION ASSAYS

(71) Applicant: CAMBRIDGE MOLECULAR DIAGNOSTICS LTD, Cambridge (GB)

(72) Inventor: Gustavo Andrés Cerda-Moya, Cambridgeshire (GB)

(73) Assignee: CAMBRIDGE MOLECULAR DIAGNOSTICS LTD., Cambridge (GB)

( * ) Notice: Subject to any disclaimer, the term of this patent is extended or adjusted under 35 U.S.C. 154(b) by 210 days.

(21) Appl. No.: 15/737,992

(22) PCT Filed: Jun. 20, 2016

(86) PCT No.: PCT/GB2016/051838
§ 371 (c)(1),
(2) Date: Sep. 13, 2018

(87) PCT Pub. No.: WO2016/203272
PCT Pub. Date: Dec. 22, 2016

(65) Prior Publication Data
US 2019/0010539 A1   Jan. 10, 2019

(30) Foreign Application Priority Data
Jun. 19, 2015   (GB) .................... 1510850.9

(51) Int. Cl.
*C12Q 1/6823* (2018.01)
*C12Q 1/682* (2018.01)
*C12Q 1/686* (2018.01)

(52) U.S. Cl.
CPC .......... *C12Q 1/6823* (2013.01); *C12Q 1/682* (2013.01); *C12Q 1/686* (2013.01);
(Continued)

(58) Field of Classification Search
CPC ........................... C12Q 1/6823; G01N 33/543
See application file for complete search history.

(56) References Cited

U.S. PATENT DOCUMENTS 6,255,051 B1   7/2001   Hammond et al.
9,791,436 B2 *   10/2017   Alexandrov ....... C07K 16/3069
(Continued)

FOREIGN PATENT DOCUMENTS

WO   199725619   7/1997
WO   2008033848   3/2008
(Continued)

OTHER PUBLICATIONS

Nallamsetty et al, EYcient site-speciWc processing of fusion proteins by tobacco vein mottling virus protease in vivo and in vitro, 2004, Protein Expression and Purification, 38,108-115 (Year: 2004).*
(Continued)

*Primary Examiner* — Narayan K Bhat
(74) *Attorney, Agent, or Firm* — Hoffmann & Baron, LLP (57) ABSTRACT

The present invention relates to a method and kit for amplifying and detecting a quantity of nucleic acid. The invention is particularly relevant to isothermal amplification techniques carried out on a flow based assay device. The amplified nucleic acid may be detected on the device using an optical read-out.

10 Claims, 6 Drawing Sheets

Specification includes a Sequence Listing.

Assay for detection of single targets (52) U.S. Cl.
CPC .. *C12Q 2563/119* (2013.01); *C12Q 2563/125* (2013.01); *C12Q 2565/518* (2013.01)

(56) References Cited

U.S. PATENT DOCUMENTS

| | | | | |
|---|---|---|---|---|
| 2003/0022225 A1* | 1/2003 | Monforte | ................. | C12Q 1/37 |
| | | | | 435/6.12 |
| 2011/0086359 A1* | 4/2011 | Babu | .................... | C12Q 1/6834 |
| | | | | 435/6.19 |
| 2016/0369338 A1* | 12/2016 | Mercolino | ........... | C12Q 1/6816 |

FOREIGN PATENT DOCUMENTS

| | | |
|---|---|---|
| WO | 2011100747 | 8/2011 |
| WO | 2012/013204 A1 | 2/2012 |

OTHER PUBLICATIONS

Kusterbeck et al., "A continuous flow immunoassay for rapid and sensitive detection of small molecules", Journal of Immunological Methods, 1990, vol. 135, No. 1-2, pp. 191-197.

Cissell et al., "Bioluminescence-Based Detect ion of MicroRNA, miR21 in Breast Cancer Cells", Anal. Chem. 2008, vol. 80, No. 7, pp. 2319-2325.

International Search Report for PCT/GB2016/051838, dated Aug. 31, 2016.

Written Opinion of the International Searching Authority for PCT/GB2016/051838, dated Aug. 31, 2016.

\* cited by examiner

Fig 1; Assay for detection of single targets

Fig 3; Strip Assay

Fig 4; Immobilized marker printed on displacement area

Fig 5; Immobilized marker printed on amplification area

Fig 6; Generation of detection zone

SEQUENCE LISTING

<160> NUMBER OF SEQ ID NOS: 11

<210> SEQ ID NO 1
<211> LENGTH: 49
<212> TYPE: DNA
<213> ORGANISM: Artificial Sequence
<220> FEATURE:
<223> OTHER INFORMATION: oligonucleotide to detect Ampicillin resistance
      gene bla

<400> SEQUENCE: 1
atctgtctat ttcgttcatc catagttgcc tgactccccg tcgtgtaga                49

<210> SEQ ID NO 2
<211> LENGTH: 49
<212> TYPE: DNA
<213> ORGANISM: Artificial Sequence
<220> FEATURE:
<223> OTHER INFORMATION: oligonucleotide to detect Kanamycin resistance
      gene kan

<400> SEQUENCE: 2
aaggacaatt acaaacagga atcgaatgca accggcgcag gaacactgc                49

<210> SEQ ID NO 3
<211> LENGTH: 49
<212> TYPE: DNA
<213> ORGANISM: Artificial Sequence
<220> FEATURE:
<223> OTHER INFORMATION: oligonucleotide to detect Chloramphenicol
      resistance gene cat

<400> SEQUENCE: 3
gcaagaatgt gaataaaggc cggataaaac ttgtgcttat ttttcttta                49

<210> SEQ ID NO 4
<211> LENGTH: 23
<212> TYPE: DNA
<213> ORGANISM: Artificial Sequence
<220> FEATURE:
<223> OTHER INFORMATION: probe for Ampicillin
<220> FEATURE:
<221> NAME/KEY: misc_feature
<222> LOCATION: (23)..(23)
<223> OTHER INFORMATION: Biotin label

<400> SEQUENCE: 4
tacgaacgat caagacagat act                                            23

<210> SEQ ID NO 5
<211> LENGTH: 23
<212> TYPE: DNA
<213> ORGANISM: Artificial Sequence
<220> FEATURE:
<223> OTHER INFORMATION: probe for Kanamycin
<220> FEATURE:
<221> NAME/KEY: misc_feature
<222> LOCATION: (23)..(23)
<223> OTHER INFORMATION: Biotin label

<400> SEQUENCE: 5
atctgtttga ctttgtcctt act                                            23

<210> SEQ ID NO 6
<211> LENGTH: 24
<212> TYPE: DNA
<213> ORGANISM: Artificial Sequence
<220> FEATURE:

```
<223> OTHER INFORMATION: probe for Chloramphenicol
<220> FEATURE:
<221> NAME/KEY: misc_feature
<222> LOCATION: (24)..(24)
<223> OTHER INFORMATION: Biotin label

<400> SEQUENCE: 6
ctactttata ttcattcttg cact                                         24

<210> SEQ ID NO 7
<211> LENGTH: 49
<212> TYPE: DNA
<213> ORGANISM: Artificial Sequence
<220> FEATURE:
<223> OTHER INFORMATION: Thiol modified oligonucleotide to Ampicillin
      resistance gene bla
<220> FEATURE:
<221> NAME/KEY: misc_feature
<222> LOCATION: (1)..(1)
<223> OTHER INFORMATION: Thiol modified

<400> SEQUENCE: 7
atctgtctat ttcgttcatc catagttgcc tgactccccg tcgtgtaga              49

<210> SEQ ID NO 8
<211> LENGTH: 49
<212> TYPE: DNA
<213> ORGANISM: Artificial Sequence
<220> FEATURE:
<223> OTHER INFORMATION: Thiol modified oligonucleotide to Kanamycin
      resistance gene kan
<220> FEATURE:
<221> NAME/KEY: misc_feature
<222> LOCATION: (1)..(1)
<223> OTHER INFORMATION: Thiol modified

<400> SEQUENCE: 8
aaggacaatt acaaacagga atcgaatgca accggcgcag gaacactgc              49

<210> SEQ ID NO 9
<211> LENGTH: 49
<212> TYPE: DNA
<213> ORGANISM: Artificial Sequence
<220> FEATURE:
<223> OTHER INFORMATION: Thiol-modified oligonucleotide to
      Chloramphenicol resistance gene cat
<220> FEATURE:
<221> NAME/KEY: misc_feature
<222> LOCATION: (1)..(1)
<223> OTHER INFORMATION: thiol modified

<400> SEQUENCE: 9
gcaagaatgt gaataaaggc cggataaaac ttgtgcttat ttttcttta              49

<210> SEQ ID NO 10
<211> LENGTH: 10
<212> TYPE: PRT
<213> ORGANISM: Artificial Sequence
<220> FEATURE:
<223> OTHER INFORMATION: artificial

<400> SEQUENCE: 10

Gly Ser Glu Thr Val Arg Phe Gln Ser Gly
1               5                   10

<210> SEQ ID NO 11
<211> LENGTH: 10
<212> TYPE: PRT
<213> ORGANISM: Artificial Sequence
```

```
<220> FEATURE:
<223> OTHER INFORMATION: artificial

<400> SEQUENCE: 11

Gly Ser Glu Asn Leu Tyr Phe Gln Ser Gly
1               5                   10
```

NUCLEIC ACID AMPLIFICATION AND DETECTION ASSAYS

CROSS REFERENCE TO RELATED APPLICATIONS

The present application is a National Stage Application claiming priority from co-pending PCT Application No. PCT/GB2016/051838 filed Jun. 20, 2016, which in turn, claims priority from Great Britain Application Serial No. 1510850.9 filed Jun. 19, 2015. Applicant claims the benefits of 35 U.S.C. § 120 as to the U.S. National Stage application and the said PCT application, and priority under 35 U.S.C. § 119 as to the said Great Britain application, and the entire disclosures of all applications are incorporated herein by reference in their entireties.

FIELD OF THE INVENTION

The present invention relates to a method and kit for amplifying and detecting a quantity of nucleic acid. The invention is particularly relevant to isothermal amplification techniques carried out on a flow based assay device. The amplified nucleic acid may be detected on the device using an optical read-out.

BACKGROUND

When performing genetic analysis, there is generally a need to amplify the number of copies in the sample, as the number present in the sample is generally too few to be detected. This can be done using, for example, thermocycling or isothermal amplification. PCR and Isothermal base amplification methods have been developed to allow the detection of low amounts of DNA or RNA. However this method can take about 90 min to generate results.

Thermocycling assays require hardware for heating and cooling as well as a means for detecting the presence of the amplified products.

Isothermal techniques include SDA, LAMP, SMAP, HDA, EXPAR/NEAR, RPA, NASBA, ICAN, SMART. The reaction proceeds at a constant temperature using strand displacement reactions. Amplification can be completed in a single step, by incubating the mixture of samples, primers, DNA polymerase with strand displacement activity, and substrates at a constant temperature. Such methods typically amplify nucleic acid copies $10^9$-$10^{10}$ times in 15-60 minutes. However the requirement remains for a means for detecting the presence of the amplified material. Standard PCR based amplification can detect 1-10 molecules per reaction after 36 cycles (90-120 min). Isothermal amplification can achieve a similar performance to PCR based technologies.

Once the nucleic acid is amplified, a nucleic acid assay requires a secondary detection technology such as spectrophotometry or turbidity. However, such known techniques have drawbacks. Fluorescence detection requires labelling to allow fluorescence, making it expensive. The reagent SYBR green binds to DNA making it inherently carcinogenic; the Ames Test shows it to be both mutagenic and cytotoxic. Also SYBR green is not specific and attaches to any double stranded DNA thus increasing background signal. Turbidity measurements require expensive instrumentation to provide quantification.

WO2011/100747 describes methods using enzymatic amplification cascade reactions. Immobilised nucleic acids strands can be made double stranded by exposure to the target nucleic acid sequences. The double stranded nucleic acids can be cleaved using restriction endonucleases which selectively cut the double stranded sequences. Several disadvantages are apparent in such a method. The sequence of the double stranded nucleic acid must contain a restriction endonuclease recognition site, and thus the choice of sequence being analysed is limited. Furthermore the double stranded material must be formed in the presence of a restriction endonuclease. It is not possible to simply add the nucleic acid test sample to the device to initiate the amplification, as further catalytic reagents in solution are also required. This requirement for an additional solution based reagent catalyst to be added to the device limits the usefulness of the device. The use of restriction enzymes to sequence specifically cleave a double stranded sample is problematic as the presence of the recognition site at any location in the sequence will trigger an unspecific cut. Thus the use of restriction enzymes may not be selective for specific sequences, as the mis-match sequences may also cause the restriction enzyme to cut the strands. Thus the use of restriction enzymes in the initial displacement step should be avoided.

An alternative molecular detection technology is the lateral flow assay, where molecules are identified via antibody interactions on a support. Lateral flow assays are well known, and have been used for decades in a variety of assay platforms, for example home pregnancy tests. The basic flow assay has been used to develop a plethora of assays for clinical, veterinary, environmental, agricultural, bio-defensive and food-born pathogen screening applications. Strip assays are copiously adaptable and as such are commercially available for an extensive range of analytes including blood protein biomarkers, mycotoxins, viral and bacterial pathogens, as well as a whole range of nucleic acid detection products. However such assays are limited by the amounts of sample required. Such assays have no amplification system, so the assays only work if sufficient amounts of the detected molecules are present in the test solution.

Since their introduction in the 1980s, lateral flow technologies have become important tools for point-of-care and home testing. They are commonly used to detect a broad array of targets such as HcG, infectious diseases and drugs of abuse and are also commonplace in veterinary testing, environmental testing and for monitoring analytes related to the human physiological condition. Initially tests provided a positive/negative result, but the development of reader technology and improvements in the materials and reagents has enabled a progression towards semi-quantitative and quantitative assays.

Lateral flow assays are essentially immunoassays which have been adapted to operate along a single axis to suit the format of a test strip. There are a number of variations of the technology that have been developed into commercial products, but they usually operate using the same basic concept. The technology is based on a series of capillary beds, such as pieces of porous paper or polymer. Each of these elements has the capacity to transport fluid, for example body fluids such as blood, saliva or urine or extracts thereof. A typical lateral flow assay test strip typically consist of the following components:

1. Sample Pad

An adsorbent pad onto which the test sample is applied. This acts as a sponge and holds an excess of sample fluid.

2. Conjugate or Reagent Pad

Once the sample pad is saturated the fluid migrates to a porous conjugate pad which contains antibodies specific to the target analyte conjugated to coloured particles (usually gold nanoparticles, or latex microspheres but in some instances fluorescent labels are used). When the sample fluid dissipates the matrix, it also dissolves the particles and in one combined, conveying action, the sample and conjugate mix flow through the porous structure. In this way, the analyte binds to the particles while migrating further along the test strip.

3. Reaction Membrane

This is typically a membrane onto which anti-target analyte antibodies are immobilised in a stripe that crosses the membrane to act as a capture zone or test line (a control zone will also be present, containing antibodies specific for the conjugate antibodies).

The reaction membrane has one or more areas (stripes) where a third molecule has been immobilized. By the time the sample-conjugate mix reaches these stripes, the analyte has been bound on the particle and the third 'capture' molecule in the stripe binds the complex. After a while, when more and more fluid has passed across the stripes, particles accumulate and the stripe-area changes color. Typically there are at least two stripes: one (the control) that captures any particle and thereby shows that reaction conditions and technology worked fine, the second contains a specific capture molecule and only captures those particles onto which an analyte molecule has been immobilized.

4. Wick or Waste Reservoir

A further absorbent pad designed to draw the sample across the reaction membrane by capillary action. After passing the test stripes the fluid enters a final porous material, which simply acts as a waste container.

The components of the test strip are usually fixed to an inert backing material and may be presented in a simple dipstick format or within a plastic casing with a sample port and reaction window showing the capture and control zones. The sensitivity of the test strip is limited by the amount of material in test solution. One molecule of the target analyte releases one antibody conjugate, with no amplification. The sensitivity of the assay is therefore limited by the concentration and volume of the sample. The present invention relates to a method to amplify the signal in a lateral flow format and allow the detection of small numbers of molecules in a short time.

SUMMARY OF THE INVENTION

The technology described herein releases a small number of molecules, which triggers an amplification of the signal inducing a cascade or "domino effect" that amplifies the signal in a near-exponential manner. No reagents are required from solution, the amplification cascade is initiated simply by applying a test sample to the device. In the following description, the term displaced refers to the process of causing release from a surface without breaking chemical bonds. Displacement is a spontaneous process caused by the presence of the target analyte, rather than a chemical reaction that requires another reagent to enable the release.

An aspect of the invention includes a device for detecting the presence of a target analyte in a fluid, the device comprising:

i) a displacement area having a first immobilised marker which can be displaced by the presence of the target analyte to produce a first released marker, wherein the displacement occurs without breaking chemical bonds;

ii) one or more signal amplification areas having further immobilised markers which can be released by the presence of the first released marker to produce a detectable marker; and iii) one or more detection areas which can identify the presence of the detectable marker;

wherein the displacement area, signal amplification area(s) and detection area(s) are connected such that fluid can flow from the detection area through the signal amplification area(s) and into the detection area(s).

An aspect of the invention includes a device for detecting the presence of a target analyte in a fluid, the device comprising:

i) a displacement area having a first immobilised marker which can be displaced by the presence of the target analyte to produce a first released marker;

ii) one or more signal amplification areas having further immobilised markers which can be released by the presence of the first released marker to produce a detectable marker; and iii) one or more detection areas which can identify the presence of the detectable marker;

wherein the displacement area, signal amplification area(s) and detection area(s) are connected such that fluid can flow from the detection area through the signal amplification area(s) and into the detection area(s).

The device can take the form of a test strip where the fluid flow occurs along a single axis. The device may also be referred to as a chip, where the strip is contained within a holder in order to aid handing of the strip. All of the chemicals and reagents required for detection of the target analyte are immobilised onto a solid support surface which is then exposed to the fluid being tested for the target analyte.

The presence of one target molecule in the displacement area produces the release of one molecule that will travel with the flow of the sample. When the released molecule (or first released marker) gets into contact with the next section, the signal amplification area, it will trigger the release of more molecules, for example 80-200 molecules each having detectable markers, that will also travel with the fluid flow and will allow the release of more molecules, for example 80-200 molecules per each molecule released on the previous step. This will produce the same reaction in the following step and so on, giving a near-logarithmic amplification in the amount of detectable marker molecules. The amplification modules can be used multiple times in series allowing high sensitivity. The cascade can be achieved by chemical cleavage of molecules, by the use of proteases or enzymatically active molecules.

Once the sample has reached the detection area, there will be enough released molecules that an enzymatic reaction or accumulation of colour reaction product can be used to detect the signal, even if the amount of target analyte applied in the fluid sample was very low.

In order to detect a single applied molecule, amplification to the marker molecules can allow for, for example, at least $10^6$ or more copies of the detectable marker. Such an amount is readily detectable. The number of detectable markers may be for example $10^8$ or higher. The number of detectable markers may be for example $10^9$ or higher. The number of detectable marker can be adjusted by the size and number of the amplification zones. Larger amplification zones mean that the sample takes longer to flow through the zone, thereby giving more time to catalyse release of the detectable markers.

The flow assay can be a lateral flow assay, where fluid flows along a strip of porous material, or a vertical flow assay where the fluid passes through various sections under gravity or capillarity. The vertical and lateral flow can be combined.

The detection can be carried out without the need for any solution reagents as everything required can be immobilised on the surface of the device. Particular applications relate to the identification of nucleic acid molecules. No further enzymes or molecules other than those immobilised are required. For example the technology allows the detection of RNA without the need for Reverse transcriptase or the detection of DNA without the need for polymerase based amplification. It also allows the detection of small amounts of other molecules such as proteins, lipids, saccharides, metabolites, small molecules and chemicals. In contrast to prior art methods, the initial displacement reaction does not require solution based catalysts. The displacement occurs without requiring cleavage of nucleic acid strands, and can thus be used to identify the presence of any chosen sequence.

In contrast to the displacement, where no chemical bonds are broken, the amplification cascade can be carried out by cleaving material from the surface via chemical bond cleavage. The chemical bond cleavage can be carried out using enzymes or other catalysts, the presence of which is only occasioned should they be displaced from the displacement area. Thus the amplification cascade can be a catalysed reaction, whereas the displacement using the target analyte is a non catalysed reaction.

The present description of this technology uses as an exemplar specific peptidases on the cascade to amplify the signal. However to achieve the same result, other enzymatically active molecules can be used such as nucleases, lipases, disaccharidases, polysaccharides, kinases, phosphorylases, methylases, sumorilases, ubiquitin deacetylases.

The present description of this technology describes the use of Horseradish Peroxidase as colorimetric detection, although other enzymes can be used to achieve the same result such as peroxidases or phosphatases. In addition, other methods can be used to visualize the accumulation of colour precipitates such as: colloidal particles, nanoparticles, chemical precipitation. In systems for quantitation where detection hardware is used, the detection could also be carried out using fluorescence, luminescence or electrical conductive molecules.

DESCRIPTION OF FIGURES

FIG. 1 shows an exemplary assay for detecting a single nucleic acid target. An oligonucleotide is immobilised to a solid support and hybridised to a strand acting as a displaceable marker (shown as Z). Exposure to the target analyte, which hybridises to the immobilised strand, causes marker Z to be released into solution. Released marker Z flows into the first amplification area (amplification zone 1). The presence of Z in solution catalyses release of marker Y via cleavage of Z' (Z' can only be cleaved by Z). Marker Y flows into amplification zone 2 where marker X is released via cleavage of Y' (Y' can only be cleaved by Y). Marker X flows into amplification zone 3 where marker E is released via cleavage of X' (X' can only be cleaved by X). Marker E flows into the detection zone where the amount of marker E released into the fluid can be analysed.

FIG. 2 shows an exemplary assay for co-detecting multiple nucleic acid targets. In the example shown, four separate oligonucleotides of different sequence (shown as target A, B, C and D) are immobilised to a solid support and hybridised to strands acting as displaceable markers (shown as Z, R, N and K respectively). Exposure to the target analyte A, which hybridises to the immobilised strand, causes marker Z to be released into solution. Exposure to the target analyte B, which hybridises to the immobilised strand, causes marker R to be released into solution. Exposure to the target analyte C, which hybridises to the immobilised strand, causes marker N to be released into solution. Exposure to the target analyte D, which hybridises to the immobilised strand, causes marker K to be released into solution. Thus all four target analytes are required in order to displace Z, R N and K into solution. The absence of one of the targets will mean than only three of the markers are displaced. The released markers flow into amplification zone 1. The presence of Z in solution catalyses release of marker Y via cleavage of Z'. The presence of R in solution catalyses release of marker Q via cleavage of R'. The presence of N in solution catalyses release of marker M via cleavage of N'. The presence of K in solution catalyses release of marker J via cleavage of K'. The up to four released markers flow into amplification zone 2, where four further markers (shown as X, P, L and H) can be released depending on the input sample. The released markers flow into amplification zone 3 In amplification zone 3, the releasable markers require two bonds to be cleaved. Thus the release of each marker is dependent on having two catalysts present. Marker W can only be cleaved if both X and P are present. Similarly marker U can only be cleaved if both L and H are present. The material flows into amplification zone 4. The presence of both W and U is required to cleave detectable marker E. Thus marker E is only released if targets A-D are all present. The fluid flows into the detection zone where the amount of marker E released into the fluid can be analysed.

DETAILED DESCRIPTION OF THE INVENTION

The technology described herein detects the presence of a small number of molecules, which occurs via a displacement event which triggers an amplification of the signal inducing a cascade or "domino effect" that amplifies the signal in every step in a near-exponential manner. The displacement event is a non-catalysed event which occurs only in the presence of the exact sequence whose presence is under evaluation.

An aspect of the invention includes a device for detecting the presence of a target analyte in a fluid, the device comprising:
i) a displacement area having a first immobilised marker which can be displaced by the presence of the target analyte to produce a first released marker;
ii) one or more signal amplification areas having further immobilised markers which can be released by the presence of the first released marker to produce a detectable marker; and
iii) one or more detection areas which can identify the presence of the detectable marker;
wherein the displacement area, signal amplification area(s) and detection area(s) are connected such that fluid can flow from the detection area through the signal amplification area(s) and into the detection area(s).

The device can take the form of a test strip where the fluid flow occurs along a single axis. The device may also be referred to as a chip, where the strip is contained within a holder in order to aid handing of the strip. All of the chemicals and reagents required for detection of the target analyte are immobilised onto a solid support surface which is then exposed to the fluid being tested for the target analyte.

The target analyte can be any molecule for which the detection is desired. The target analyte can be a nucleic acid. The target analyte can be DNA, RNA or modified forms thereof. The nucleic acid, DNA or RNA may be derived directly from an organism, for example a virus, bacteria or other pathogen. The nucleic acid may be mammalian. The method allows the specific detection of particular sequences, depending on the choice of displacement method. The target analyte nucleic acid strand may be single stranded or double stranded.

The displacement may be carried out by disrupting the binding of a double stranded nucleic acid where one of the two strands is immobilised. Such disruption results in the immobilisation of the target analyte via the formation of a duplex, and release of a first released marker, the first released marker being the non-immobilised strand or a fragment thereof. Thus the first immobilised marker may be a single nucleic acid strand. Alternatively the first immobilised marker may be a single nucleic acid strand which is in part double stranded and in part single stranded. The first immobilised marker may be a partly double stranded nucleic acid.

The single stranded region of the immobilised marker may be used to sequence selectively capture the target analyte. Thus the sequence specificity of the assay comes from only the correct target sequence being captured by the immobilised marker. The capturing of the analyte gives rise to displacement of the partly double stranded section, thereby releasing a detectable marker into solution. Thus the detectable marker is only released when the correct sequence is hybridised.

For non-nucleic acid based target analytes, the release can be triggered by the displacement of an antibody/antigen, peptide/peptide or peptide/molecule interaction. For example if copies of the target analyte are already immobilised to the surface, and conjugated to antibodies, exposure to the target analytes in solution causes the antibodies to be released from the surface via binding to the molecules in solution. The strength of the antibody/target interaction depends on the nature of the antibody, but can be adjusted as needed via control of the buffer conditions such as pH and ionic strength, and also via temperature. Similar immunoassays are well known in applications such as hormone testing, glucose testing etc. Conditions for the release of particular detectable markers can be designed based on the target analyte. The released marker may contain an antibody bound to the target analyte.

Further examples of possible displacement mechanisms include the disruption of protein-protein interaction: one protein bound to the probe (printed) and the other protein coupled to first cleavage molecule. The presence of the target in the sample will disrupt the interaction with the printed molecule, which displaces the first released molecule to the amplification zone. Targets that can be detected by this method could be any molecule (organic or inorganic) that disrupt interaction between two molecules.

Upon addition of a target sample to the device, the sample flows, either via capillary action or gravity directly into the displacement zone. The presence of the analyte causes release into solution of the first released marker. In the absence of the target analyte, the first marker is not released, and is therefore unable to flow into the amplification zone.

Immobilisation of the first marker may be by any interaction which is stable to the flow of liquid. The immobilisation may be covalent or may be via a non-covalent interaction, such as for example an ionic interaction or a stable physical binding interaction such as biotin/avidin. The immobilisation of oligonucleotides may be via UV-cross-linking.

Release of the first released marker allows the amplification process to start. The first released marker may contain a catalyst for use in the amplification zone. The catalyst may be for example an enzyme which can catalyse multiple events in the amplification zone(s). The first released marker may therefore contain an enzyme. The enzyme may be, for example a protease or peptidase.

The device may contain more than one amplification zone. For example the device may contain three or more signal amplification areas. Each amplification area may be carrying out the same transformation, or different amplification processes may be carried out in each zone. For example the first displacement reaction may result in catalyst Z being released into solution. The first amplification zone may contain a catalyst Y immobilised by group Z' (i.e. cleavable by Z). Exposure to Z thereby releases Y in the first amplification zone. After flow through the amplification zone, there are more molecules of Y is solution than there were molecules of Z entering the amplification zone. A second amplification zone can be present where catalyst X is immobilised by Y'. Exposure to released catalyst Y, which cleaves Y', releases X. A further amplification zone can be present where catalyst W is immobilised by X'. Thus many more copies of W are released in the final amplification zone than copies of Z were present initially. Thus the amplification occurs.

In the example given above, molecule W can be detected, or cause a detectable event to occur. Additionally, optionally X, Y or Z can each carry the same detectable moiety or cause the same detectable event to occur Alternatively each of W, X, Y and Z can each carry the same detectable moiety or cause the same detectable event to occur.

Where the device contains more than one amplification zone, the detectable marker can be released in each amplification zone, or just the final amplification zone. A device may contain
i) a displacement area having a first immobilised marker which can be displaced by the presence of the target analyte to produce a first released marker;
ii) a first signal amplification area having further immobilised markers which can be released by the presence of the first released marker to produce a second released marker;
iii) a second amplification area having further immobilised markers which can be released by the presence of the second released marker to produce a detectable marker; and
iv) one or more detection areas which can identify the presence of the detectable marker;
wherein the displacement area, signal amplification area(s) and detection area(s) are connected such that fluid can flow from the detection area through the signal amplification area(s) and into the detection area(s).

The displacement process is a non-catalysed process that occurs without breaking chemical bonds.

The device may contain further amplification areas, each capable of amplifying the signal and releasing further markers. A third amplification area may be present, in which case the second amplification area can release a third released marker, or further copies of the second or first released markers. The third amplification area releases the detectable marker, although the first, second or third markers may also be detectable.

The amplification areas contain immobilised probes or markers which can be released upon exposure to the first, second or further marker(s). Immobilisation of the probes or further markers may be by any interaction which is stable to the flow of liquid. The immobilisation may be covalent or may be via a non-covalent interaction, such as for example an ionic interaction or a stable physical binding interaction such as biotin/avidin. The further probes/markers contain a portion which can be released from the surface by the presence of the first released marker to produce a detectable marker which is free in solution.

The immobilised probes contain a cleavage element. Any catalyst which causes release of bound material via cleavage of the cleavage element can be used as part of the amplification system. Suitable catalysts include:

Enzymatic mediated cleavage such as:
Polysaccharide hydrolases such as maltase, glucosidase, amylase, sucrase which cleave polysaccharide chains.
Carboxylesterases, commonly found in the liver, such as acetylcholineesterase, carboxylesterase 1, 2 and 3.
Thiolases from the mevalonate pathway prodoce acetyl-coa and fatty acids upon cleavage.
Lipases that hydrolyze fatty acids, such as lysosomal lipase and gastric lipase.
Deoxyribonucleases that catalyze the hydrolytic cleavage of the phosphodiester bond in nucleic acids, producing free nucleotides.
Phosphatases cleaving phosphate groups of proteins.
Deubiquitinating enzymes cleaving ubiquitin molecules of proteins.
Nuclease mediated cleavage such as:
Isomerases, deoxyribonucleases, such as deoxyribonuclease I, deoxyribonuclease II, Micrococcal nucleases, endonucleases, exonucleases
Restriction enzymes type I, II, Iii, IV, V or artificial restriction enzymes, that cut DNA,
Ribonucleases:
a. endoribonucleases (RNase A, RNase H, RNase III, RNaseL, RNaseP, RNase PhyM, RNase T1, RNaseT2, RNase U, RNase V).
b. exoribonucleases (Polynucleotide Phosphorylase (PNPase), RNase PH, RNase R, RNase D, RNase T, Oligoribonuclease, Exoribonuclease I, Exoribonuclease II j.

The immobilised markers may therefore include a cleavage element selected from an amide bond, a carbohydrate moiety, a dinucleotide, an ester moiety, a thioester moiety or a particular nucleotide sequence.

The ratio of the first released marker to the detectable marker can be at least 1/1000. In order to detect the applied molecule, amplification to the marker molecules can allow for, for example, at least $10^6$ or more copies of the detectable marker released into solution. Such an amount is readily detectable. The number of detectable markers may be for example $10^8$ or higher. The number of detectable markers may be for example $10^9$ or higher. The number of detectable marker can be adjusted by the size and number of the amplification zones. Larger amplification zones mean that the sample takes longer to flow through the zone, thereby giving more time to catalyse release of the detectable markers.

Each of the released products can carry the same detectable marker. The detectable marker may be for example an enzyme. The enzyme may for example cause a colour change in the detection zone. The detectable marker may carry a detectable label. The detectable marker may be for example a colloidal or nanoparticle stained molecule. The detectable label may be a fluorescent label. The detectable label may be a luminescent molecule. The nanoparticles may be gold, iron, copper, silver or similar metallic particles.

The detection may result in the direct identification of released material. Alternatively the detection may be carried out using a colourimetric assay. The colourimetric assay may use the released enzyme to cause the colour change. The enzyme may cause luminescence or fluorescence or may result in a simple colour change.

Suitable colourimetric assays include peroxidase assays (for example using HRP), galactosidase assays (for example using a Beta-galactosidase) or alkaline phosphatase (for example using alkaline phosphatase). The released enzyme may therefore be horseradish peroxidase (HRP), galactosidase or alkaline phosphatase.

The measurement may be a simple end point detection (is the target analyte present; yes or no), or may involve an element of quantitative analysis. For quantitative analysis, the device can be coupled to a suitable reader allowing a direct measurement of the signal intensity in the detection zone. This can be correlated to the number of molecules present in the target sample. For semi-quantitative analysis, the detection zone can be calibrated to bind different amounts of colour particles (for example gold colloidal stained protein, bound to a printed antibody).

For end point or semi-quantitative detection, the detection can be carried out using the human eye, rather than requiring any further hardware to read the result.

The detection can be carried out in multiple zones or lines. For example, for semi quantitative detection different lines with different amount of trapping molecules can be printed (e.g. a first line containing 25 ng/cm, a second line containing 250 ng/cm, a third line containing 2.5 µg/cm and so on). Therefore, considering the molecular weight of the trapping molecule and calibrating the amplification steps, the accumulation of color on the stripes will be a reflection of the amount of target on the sample (i.e. if sample contains 1-10 target molecules, only first line will accumulate the color. If sample contains 10-100 target molecules, first and second lines will accumulate the color. If sample contains 100-1,000 target molecules, first, second and third lines will accumulate the color etc. Thus the quantification can be carried out using the different bands where the different bands have different responses depending on the amount of detectable marker in the fluid.

Also disclosed herein is a method of detecting a target analyte, the method comprising applying a sample to a device having
i) a displacement area having a first immobilised marker which can be displaced by the presence of the target analyte to produce a first released marker;
ii) one or more signal amplification areas having further immobilised markers which can be released by the presence of the first released marker to produce a detectable marker; and
iii) one or more detection areas which can identify the presence of the detectable marker;
wherein the displacement area, signal amplification area(s) and detection area(s) are connected such that fluid can flow from the detection area through the signal amplification area(s) and into the detection area(s); flowing the sample from the detection area through the signal amplification area(s) and into the detection area(s) and determining from the presence of the detectable marker in the detection area the presence of the target analyte in the sample.

The method requires no further material in solution. No enzymes or other catalysts are required to cause displacement.

Also disclosed herein is a method of detecting a target analyte, the method comprising applying a sample to a device having
i) one or more displacement areas having one or more immobilised markers which can be displaced by the presence of the one or more target analytes to produce one or more first released markers;
ii) one or more signal amplification areas having further immobilised markers which can be released by the presence of the first released marker(s) to produce one or more detectable markers; and
iii) one or more detection areas which can identify the presence of the detectable marker(s);
wherein the displacement area(s), signal amplification area(s) and detection area(s) are connected such that fluid can flow from the detection area(s) through the signal amplification area(s) and into the detection area(s); flowing the sample from the detection area(s) through the signal amplification area(s) and into the detection area(s) and determining from the presence of the detectable marker(s) in the detection area the presence of the target analyte in the sample.

The sensitivity and/or specificity of the assay can be improved by detecting more than one target analyte on the same device. More than one target may refer to, for example, different regions of the same gene or pathogen or may refer to, for example, two or more different pathogens. Detection of more than one target to trigger the detectable signal can be used to detect for example more than one part of a target gene or pathogen.

The detection of separate target analytes may be carried out using independent amplification cascades for each target. Amplifications can be linked to release only one detectable molecule in the last step of the cascade, the final release being dependent on the presence of markers caused by the presence of both target analytes. Therefore signal will only be generated and detected in the presence of the different targets in the same sample. The use of displacement and amplification cascades for multiple regions of the same target gene or pathogen can achieve a greater accuracy than qPCR.

As with the device, the target analyte can be a nucleic acid. The nucleic acid can have any of the properties describes above in connection with the device.

Also disclosed is a kit of reagents for detecting a target analyte, the kit containing a device as described above and a buffer solution into which a biological sample can be added. The kit may further include instructions for use of the kit.

Uses or Application of the Present Technology

Any biological sample can be analysed. Suitable fluids for application to the device include saliva, blood, plasma, urine, sweat etc. Samples may be lysed prior to analysis. Suitable solid sample may be dissolved in buffers prior to analysis.

The present technology can be use for fast detection of the presence of many target analytes, for example interleukins, hormones, oncogenes, as protein or nucleic acids, pathogens (as protein or nucleic acid), virus (as protein or nucleic acid), drugs, toxins, metabolites.

Fields in which the technology may be used include pathogen identification and contaminant tracing; forensic analyses; food industry; soil analyses; agriculture; aquaculture etc.

Experimental Details & Methods:
Generation of lateral flow devices for nucleic acid identification:
Printing Immobilized Marker on Displacement Area:
Strips of Positive charger Nylon membrane (e.g. Thermo scientific Cat #77016; Roche Cat #11417240001) were cut using clean scissors (e.g. strips of 15×80 mm).

Reverse and complementary oligonucleotides (nucleic acid oligonucleotide) were designed to hybridize the target sequence (e.g. 49 base single strand DNA oligonucleotide, for example to detect: Ampicillin resistance gene bla 5'-ATCTGT CTATTTCGTTCATCCAT-AGTTGCCTGACTCCCCGTCGTGTAGA (SEQ ID NO: 1); Kanamycin resistance gene kan 5'-AAGGACAATTA-CAAACAGGAATCGAATGCAACCGGCGCAG-GAACACTGC (SEQ ID NO: 2); Chloramphenicol resistance gene cat 5'-GCAAGAATGTGAATAAAGGCCGGATAA AACTTGTGCTTATTTTTCTTTA (SEQ ID NO: 3)). The 49 base single stranded oligonucleotide was diluted to 0.25 µg/µl (approximately 15 µM) in printing solution (0.4 N NaOH in double distilled water).

Oligonucleotides were printed using flat guide (e.g ruler or glass slip). Oligonucleotides in printed solutions were spread on the edge of the guide (e.g. 2.5 µl/cm of oligonucleotides in printing solution) and printed as a stripe in the middle of the 80 mm axis (e.g. leaving 7.5 mm on each side). The membranes were dried and further cross-linked using UV light (e.g. Stratalinker 2400). Membranes were blocked by incubating 1 hour in 2% BSA diluted in TBST (50 mM Tris pH 7.4, 150 mM NaCl, 0.05% tween-20) with constant agitation. Membranes were washed 4 times for 5 min in TBST.

The single stranded displaceable probe carrying a detectable label (e.g. Biotin) was designed to partially hybridize to the printed probe (e.g. Tm 25-35° C., for example displaceable probe for: Ampicillin 5'-tacGAACGAtcaAGACAGA-Tact[Biotin] (SEQ ID NO: 4); Kanamycin 5'-atcTGTTTGactTTGTCCTTact[Biotin] (SEQ ID NO: 5); Chloramphenicol 5'-ctaCTTTATattCATTCTTGCact[Biotin] (SEQ ID NO: 6)). The displaceable probe was diluted to 1 µM in TBST (e.g. 2 ml). Printed membranes were hybridized with displaceable probe at 42° C. overnight with constant movements. Membranes were washed 4 times for 5 min in TBST.

Coupling of the catalyst to the displaceable probe. The printed membranes coupled with displaceable label probe, were incubated 2-4 hours in TBST containing 2% BSA plus the first enzymatically active molecule at 5 µg/ml (e.g. Avidin-protease Z, for example Avidin-Tobacco Vein Mottling Virus (TVMV) protease). Membranes were washed 4 times 5 min in TBST. Membranes were cut into four strips and then freeze dried for storage.
Alternatively
Strips of Positive charger Nitrocellulose membrane (e.g. Sartorius Unistart CN95, CN140, CN150) were cut using clean scissors (e.g. strips of 15×80 mm). Reverse and complementary Thiol-modified oligonucleotides (e.g. Ampicillin resistance gene b/a 5'-[Thiol] ATCTGTCTAT-TTCGTTCATCCATAGTTGCCTGACTCCC CGTCGTGTAGA (SEQ ID NO: 7); Kanamycin resistance gene kan 5'-[Thiol]AAGGACA ATTACAAACAG-GAATCGAATGCAACCGGCGCAGGAACACTGC (SEQ ID NO: 8); Chloramphenicol resistance gene cat 5'-[Thiol] GCAAGAATGTGAATAAAGGCCGGA-TAAAACTTGTGCTTATTTTTCTTTA (SEQ ID NO: 9)) where linked to Maleimide-activated BSA.

Oligonucleotides-BSA were diluted in PBS at 2 µg/µl and printed using flat guide (e.g ruler or glass slip). Oligonucleotides in printed solutions were spread on the edge of the guide (e.g. 2.5 µl/cm of oligonucleotides in printing solution) and printed as a stripe in the middle of the 80 mm axis (e.g. leaving 7.5 mm on each side). The membranes were dried and the membranes were blocked by incubating 1 hour in 2% BSA diluted in TBST (50 mM Tris pH 7.4, 150 mM NaCl, 0.05% tween-20) with constant agitation. Membranes were washed 4 times for 5 min in TBST.

The single stranded displaceable probe carrying a detectable label (e.g. Biotin) was designed to partially hybridize to the printed probe (e.g. Tm 25-35° C., for example displaceable probe for: Ampicillin 5'-tacGAACGAtcaAGACAGA-Tact[Biotin] (SEQ ID NO: 4); Kanamycin 5'-atcTGTTTGactTTGTCCTTact[Biotin] (SEQ ID NO: 5); Chloramphenicol 5'-ctaCTTTATattCATTCTTGCact[Biotin] (SEQ ID NO: 6)). The displaceable probe was diluted to 1 µM in TBST (e.g. 2 ml). Printed membranes were hybridized with displaceable probe at 42° C. overnight with constant movements. Membranes were washed 4 times for 5 min in TBST.

Coupling of the catalyst to the displaceable probe. The printed membranes coupled with displaceable label probe, were incubated 2-4 hours in TBST containing 2% BSA plus the first enzymatically active molecule at 5 µg/ml (e.g. Avidin-protease Z, for example Avidin-Tobacco Vein Mottling Virus (TVMV) protease). Membranes were washed 4 times 5 min in TBST. Membranes were cut into four strips and then freeze dried for storage.

Printing Immobilized Marker on Amplification Area:

Similarly as described above, stripes of membrane (e.g. Positive charger Nylon or Nitrocellulose) were cut using clean scissors (e.g. stripes of 15×80 mm).

The labeled substrate (e.g. Biotinylated peptide BSA biotin) was printed along middle of the 80 mm axis (e.g. leaving 7.5 mm in each side). Considering the amount of labeled substrate and the binding capacity of the membrane (e.g. Nitrocellulose allow 170-200 µm/cm$^2$ of protein) the level of amplification per step can be adjusted by varying the width of the printed area. Printed membranes were blocked by incubating 1 hour with 2% BSA diluted in TBST with constant agitation. Membranes were washed 4 times for 5 min in TBST.

The printed membranes were incubated 2-4 hours in TBST containing 2% BSA plus first enzymatically active molecule at 5 µg/ml (e.g. Avidin-Z'-protease Y, for example Avidin-GSETVRFQSG-Tobacco Etch Virus (TEV) protease) (SEQ ID NO: 10). Membranes were washed 4 times for 5 min in TBST. Membranes were cut into four strips and then freeze dried for storage.

Using this procedure, membranes carrying other steps of amplification were made (e.g. Avidin-Y'-protease_X, Avidin-X'-enzyme_E, etc). For the last amplification step, an enzyme (e.g. Avidin-GSENLYFQSG-HRP (SEQ ID NO: 11)) or colloidal stained molecule (e.g. Avidin-GSEN-LYFQSG-GFPgold (SEQ ID NO: 11) or Avidin-GSEN-LYFQSG-HRPgold (SEQ ID NO: 11)) was used.

For detection of multiple targets at the last amplification step, an enzyme flanked by binding molecules at the amino and carboxyl terminus (e.g. Avidin-GSENLYFQSG-HRP (SEQ ID NO: 11)-GSETVRFQSG-Avidin (SEQ ID NO: 10)) or colloidal stained molecule (e.g. Avidin-GSEN-LYFQSG-GFPgold (SEQ ID NO: 11)-GSETVRFQSG-Avidin (SEQ ID NO: 10) or Avidin-GSENLYFQSG-HRPgold (SEQ ID NO: 11)-GSETVRFQSG-Avidin (SEQ ID NO: 10)) was used.

Generation of Detection Zone:

Similarly as described above, stripes of membrane (e.g. Whatman filter paper or Nitrocellulose) were cut using clean scissors (e.g. stripes of 50×80 mm).

For enzymatic colourimetric detection end point detection, Whatman filters were printed with colourimetric substrate (e.g. TMB for HRP). For example, TMB solution (e.g. 10 µl/cm of solution containing 0.5 mg/ml of 3,3',5,5' Tetramethyl Benzidine; 2.5 mg/ml Sodium Nitroprusside dehydrate, 50% DMSO in water) was printed along the 80 mm axis (e.g. leaving 10 and 40 mm distance from the side) for HPR detection. Membranes were let dry and were cut into 50 mm strips.

For end-point detection or semi quantitative detection molecules that trap a stained molecule were printed (e.g. anti-HRP antibody that bind gold colloidal stained HRP). A line of anti-HRP antibody (e.g. 1 µg/cm affinity pure rabbit anti-horseradish peroxidase Jackson cat #323-005-021) was printed along the 80 mm axis (e.g. leaving 10 and 40 mm distance from the sides). For semi quantitative detection different lines with different amount of trapping molecules were printed (e.g. first line containing 25 ng/cm, second 250 ng/cm, third 2.5 µg/cm, fourth 25 µg/cm and so on). Therefore, considering the molecular weight of the printed molecule (e.g. rabbit anti-horseradish peroxidase molecular weight is 160 kD, therefore the printed bands will be 9.2×10$^{10}$, 9.2×10$^{11}$, 9.2×10$^{12}$ and 9.2×10$^{13}$ molecules/cm respectively, which can bind 1.8×10$^{11}$, 1.8×10$^{12}$, 1.8×10$^{13}$ and 1.8×10$^{14}$ released molecules respectively) and calibrating the amplification steps (e.g. if the total amplification is 10$^{11}$), the accumulation of color on the stripes will be a reflection of the amount of target on the sample (i.e. if sample contains 1-10 target molecules, only first line will accumulate the color. If sample contains 10-100 target molecules, first and second lines will accumulate the color. If sample contains 100-1,000 target molecules, first, second and third lines will accumulate the color. If sample contains 1,000-10,000 target molecules, first, second, third and fourth lines will accumulate the color). Printed membranes were blocked by incubating 1 hour with 2% BSA diluted in TBST with constant agitation. Membranes were washed 4 times 5 min in TBST. Membranes were cut into four strips and then freeze dried for storage.

Figure 1:
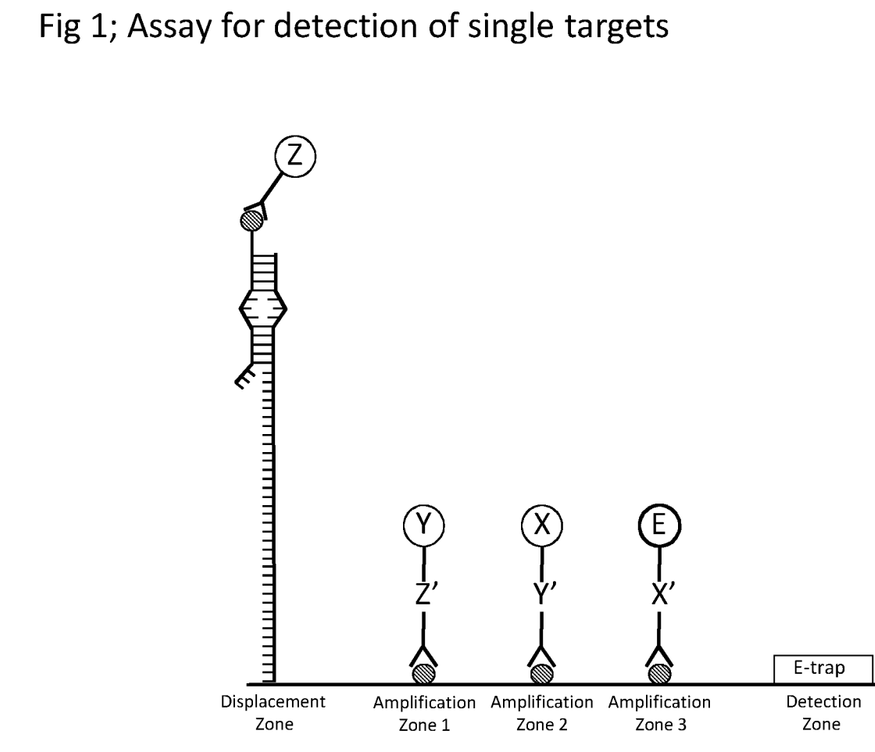
Figure 2:
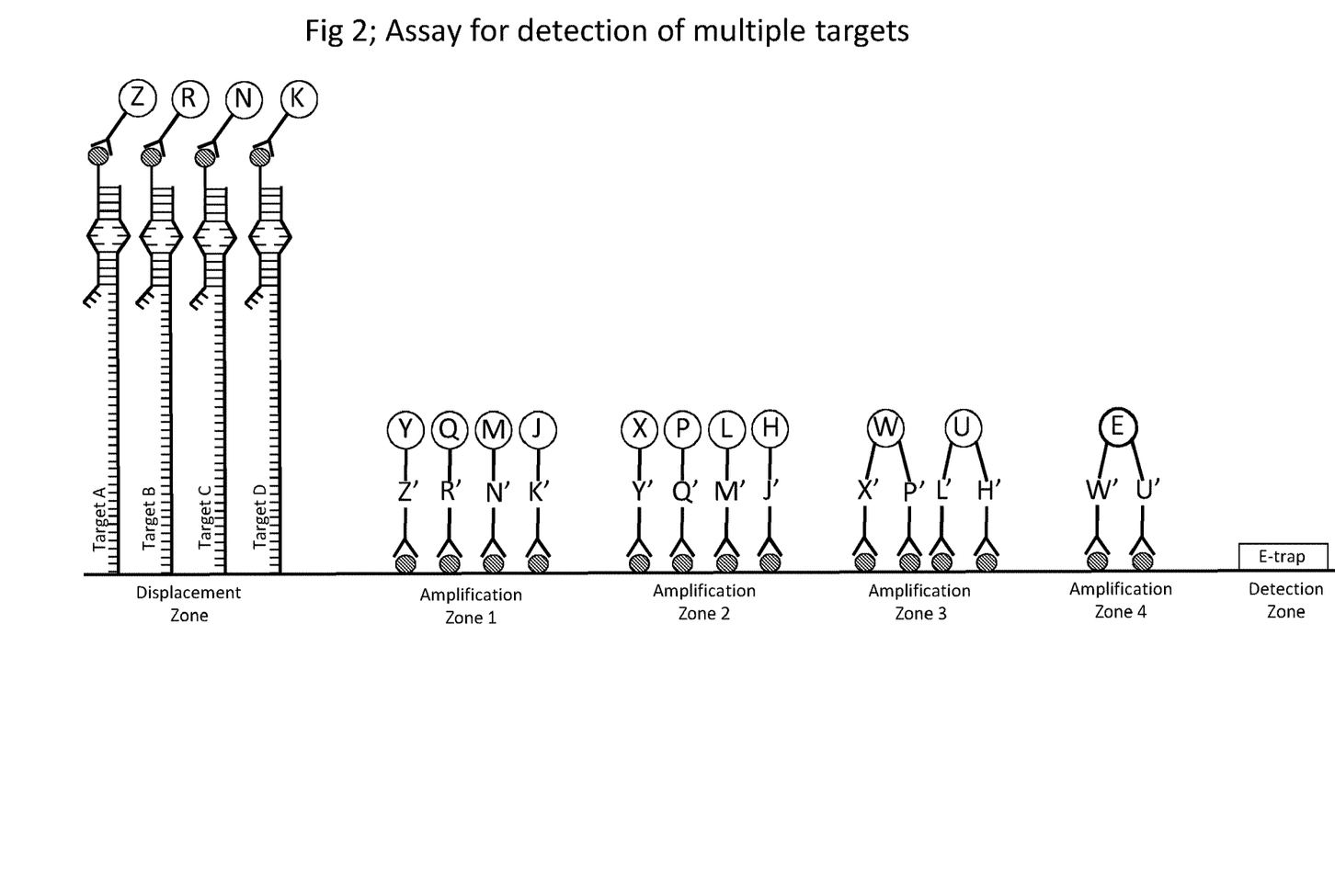
Figure 3:
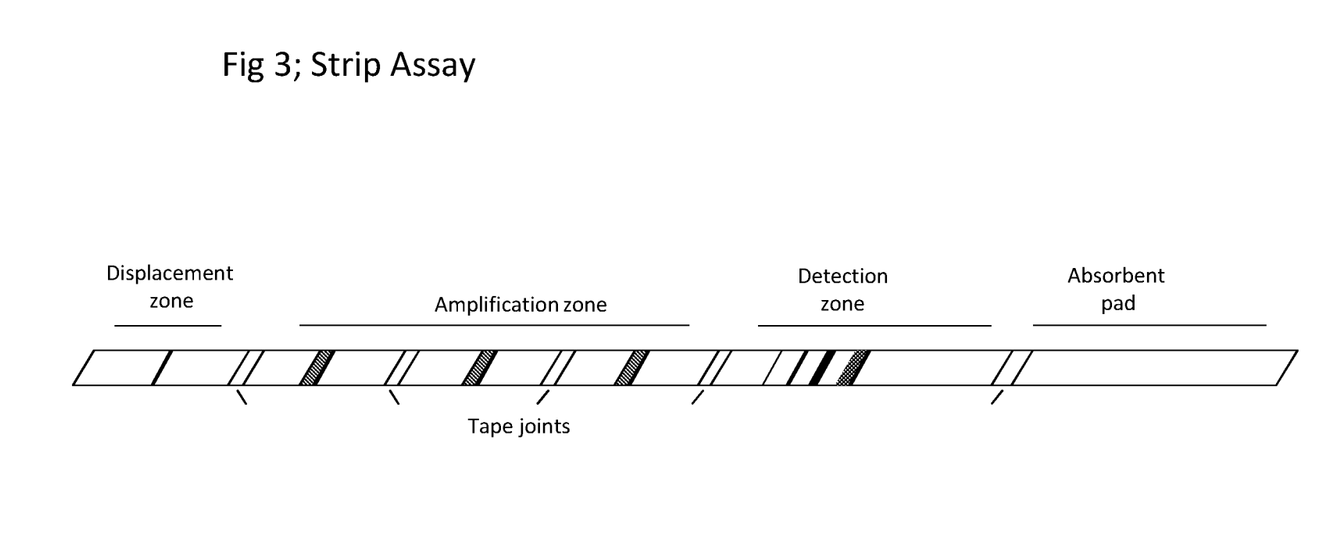
FIG. 3 shows the assay in strip format. The sample flows from the displacement zone, through the amplification zone, through the detection zone and into the absorbent pad.
Figure 4:
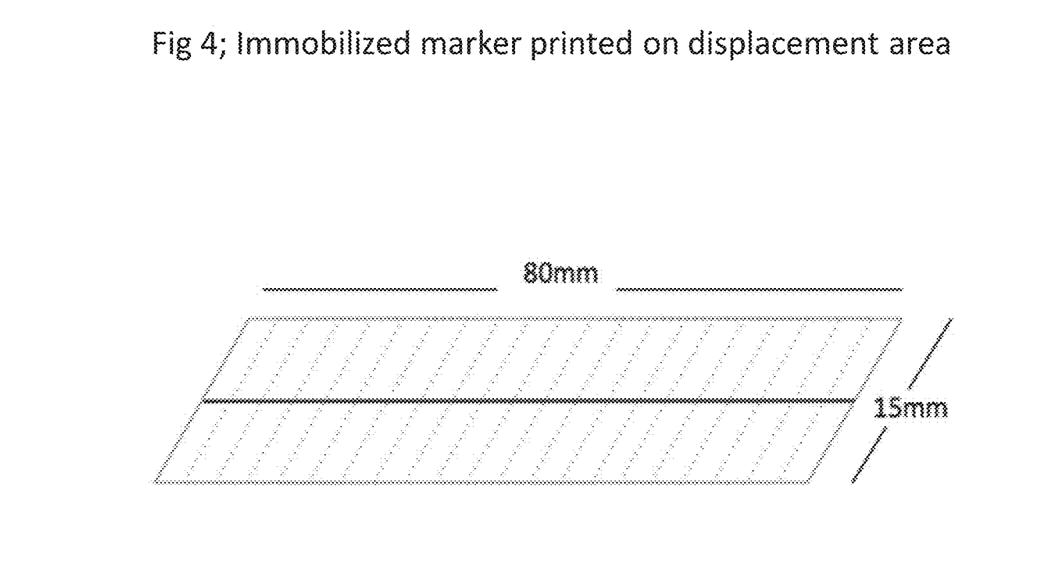
FIG. 4 shows immobilized marker printed on the displacement zone of the strip assay of FIG. 3.
Figure 5:
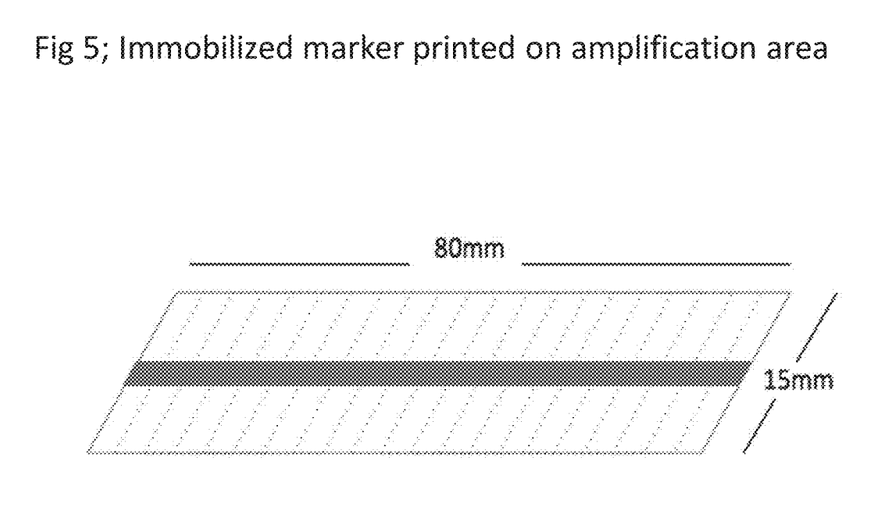
FIG. 5 shows immobilized marker printed on an amplification zone of the strip assay of FIG. 3.
Figure 6:
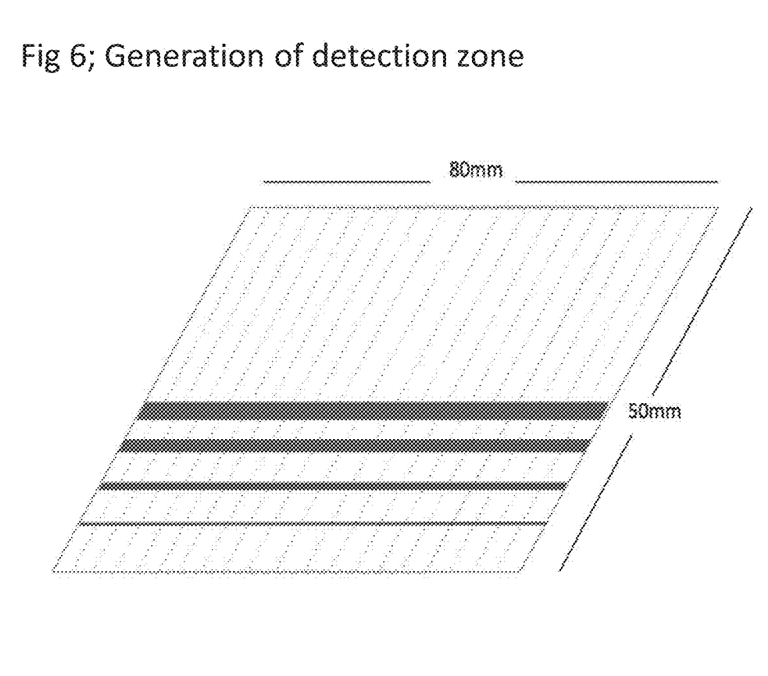
FIG. 6 shows generation of the detection zone of the strip assay of FIG. 3.

Assembly of Lateral Flow Assay as Shown in FIG. 3:

Each of the different sections (displacement, amplification and detection zones) of the assay were joined forming a line using small strip of tape to merge the junctions (e.g. scotch invisible tape). At the end of the detection zone a pad of absorbent material was added glass fiber paper.

Performing the Assay:

Sample was diluted in TBST buffer and applied to the assay strip. The sample travels through capillarity along the assay strip. In the displacement zone, the target hybridizes to the single stranded region of the immobilized probe, causing displacement of the oligonucleotide-biotin-avidin-protease marker. This flows into the amplification zone, thereby cleaving the peptide linkage between the avidin and the second protease to release the second protease. The second protease flows into the final amplification zone, where the second protease causes the HRP to be released. The HRP flows into the detection zone where its presence can be quantified.

The invention claimed is:

1. A test strip device for detecting the presence of a target nucleic acid analyte in a fluid applied to the device, the device comprising:
   i) a displacement area having a first immobilised marker which can be displaced by the presence of the target nucleic acid analyte to produce a first released marker, wherein the first released marker comprises a protease, wherein the protease is either Tobacco Etch Virus (TEV) protease or Tobacco Vein Mottling Virus (TVMV) protease;
   ii) a signal amplification area having further immobilised markers or detectable markers, each comprising a peptide linkage which can be released by the presence of the TEV or TVMV protease;
   iii) optionally one or more further signal amplification areas having further immobilised markers which can be released by the presence of a released marker, wherein one or more of the signal amplification areas releases a detectable marker; and
   iv) one or more detection areas which can identify the presence of any of the detectable markers released from the signal amplification area or areas;
   wherein the displacement area, signal amplification area(s) and detection area(s) are connected on a porous material such that fluid can flow from the displacement area through the signal amplification area(s) and into the detection area(s) upon application of the fluid to the device.

2. The device according to claim 1 wherein the first immobilised marker is a partly double stranded nucleic acid.

3. The device according to claim 1 wherein the device contains three or more signal amplification areas.

4. The device according to claim 1 wherein the detectable marker contains an enzyme.

5. The device according to claim 1 wherein the detectable marker carries a detectable label.

6. The device according to claim 1 wherein the detection area performs a colourimetric assay.

7. The device according to claim 6 wherein the colourimetric assay uses an enzyme or gold nanoparticles.

8. A kit of reagents for detecting a target nucleic acid analyte, the kit containing a device according to claim 1 and a buffer solution into which a biological sample can be added.

9. The device according to claim 1 wherein the porous material is nitrocellulose.

10. A method of detecting a target nucleic acid analyte, the method comprising applying a sample to a test strip device having
    i) a displacement area having a first immobilised marker which can be displaced by the presence of the target nucleic acid analyte to produce a first released marker, wherein the first released marker comprises a protease, wherein the protease is either Tobacco Etch Virus (TEV) protease or Tobacco Vein Mottling Virus (TVMV) protease;
    ii) a signal amplification area having further immobilised markers or detectable markers, each comprising a peptide linkage which can be released by the presence of the TEV or TVMV protease;
    iii) optionally one or more further signal amplification areas having further immobilised markers which can be released by the presence of a released marker, wherein one or more of the signal amplification areas releases a detectable marker; and
    iv) one or more detection areas which can identify the presence of any of the detectable markers released from the signal amplification area or areas;
    wherein the displacement area, signal amplification area(s) and detection area(s) are connected such that fluid can flow from the displacement area through the signal amplification area(s) and into the detection area(s); flowing the sample from the displacement area through the signal amplification area(s) and into the detection area(s) and determining from the presence of the detectable marker in the detection area the presence of the target nucleic acid analyte in the sample.

* * * * *